United States Patent [19]

Stoltefuss et al.

[11] Patent Number: 5,514,803
[45] Date of Patent: May 7, 1996

[54] 2,6-DISUBSTITUTED 4-QUINOLYL-DIHYDROPYRIDINES

[75] Inventors: Jürgen Stoltefuss, Haan; Siegfried Goldmann, Wuppertal; Alexander Straub, Wuppertal; Martin Bechem, Wuppertal; Rainer Gross, Wuppertal; Siegbert Hebisch, Bottrop; Joachim Hütter, Wuppertal; Howard-Paul Rounding, Wuppertal, all of Germany

[73] Assignee: Bayer Aktiengesellschaft, Leverkusen, Germany

[21] Appl. No.: 230,178

[22] Filed: Apr. 20, 1994

[30] Foreign Application Priority Data

Apr. 27, 1993 [DE] Germany .................. 43 13 691.5

[51] Int. Cl.$^6$ .................. C07D 403/02; A61K 31/47
[52] U.S. Cl. .................. 546/167
[58] Field of Search .................. 546/167; 514/314

[56] References Cited

U.S. PATENT DOCUMENTS

| | | | |
|---|---|---|---|
| 4,145,432 | 3/1979 | Sato | 424/266 |
| 4,248,873 | 2/1981 | Bossert et al. | 424/286 |
| 5,100,900 | 3/1992 | Stoltefuss et al. | 514/314 |
| 5,204,472 | 4/1993 | Stoltefuss et al. | 546/168 |

FOREIGN PATENT DOCUMENTS

| | | |
|---|---|---|
| 0071819 | 2/1983 | European Pat. Off. . |
| 0451654 | 10/1991 | European Pat. Off. . |
| 0452712 | 10/1991 | European Pat. Off. . |
| 0515940 | 12/1992 | European Pat. Off. . |
| 0518105 | 12/1992 | European Pat. Off. . |
| 0538690 | 4/1993 | European Pat. Off. . |

*Primary Examiner*—David B. Springer
*Attorney, Agent, or Firm*—Sprung Horn Kramer & Woods

[57] ABSTRACT

The invention relates to new 2,6-disubstituted 4-quinolyl-dihydropyridines

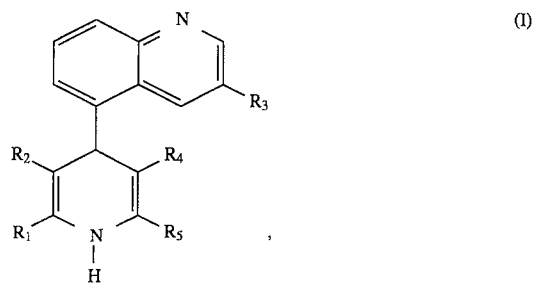

(I)

in which $R_1$ to $R_5$ have the meaning indicated in the description, processes for their preparation and their use in medicaments, in particular in compositions for the treatment of cardiovascular disorders.

5 Claims, No Drawings

2,6-DISUBSTITUTED 4-QUINOLYL-DIHYDROPYRIDINES

The invention relates to new 2,6-disubstituted 4-quinolyl-dihydropyridines, processes for their preparation and their use in medicaments, in particular in compositions for the treatment of cardiovascular disorders.

It is already known that 1,4-dihydropyridines have vasodilating properties and can be used as coronary agents and anti-hypertensives. It is furthermore known that 1,4-dihydropyridines cause an inhibition of the contractility of smooth and cardiac muscles and can be employed for the treatment of coronary and vascular disorders. 4-Quinolyl-dihydropyridines which have a positively inotropic action are also already known from U.S. Pat. No. 5,100,900.

With the knowledge of the prior art, it could not be foreseen that the compounds according to the invention would affect the contractility of the heart and can therefore be used for the control of cardiovascular disorders.

The present invention relates to new 2,6-disubstituted 4-quinolyl-dihydropyridines of the general formula (I)

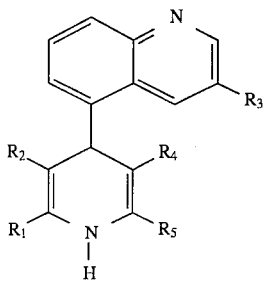

in which $R^1$ and $R^5$ are identical or different and represent hydrogen, cyano, formyl, trifluoromethyl or straight-chain or branched alkyl having up to 8 carbon atoms, which is optionally substituted by hydroxyl, straight-chain or branched alkoxy or alkoxycarbonyl in each case having up to 8 carbon atoms or by a group of the formula $-NR^6R^7$, $-O-CO-R^8$, $-O-(CH_2)_a-OR^{8'}$ or $-O-(CH_2)_{a'}-NR^9R^{10}$, in which $R^6$, $R^7$, $R^9$ and $R^{10}$ are identical or different and denote hydrogen, phenyl or straight-chain or branched alkyl having up to 6 carbon atoms, $R^8$ and $R^{8'}$ are identical or different and denote straight-chain or branched alkyl having up to 6 carbon atoms, and $a$ and $a'$ are identical or different and denote a number 2, 3, 4 or 5, $R^2$ represents nitro, cyano or formyl, or $R^1$ and $R^2$ together form a lactone ring of the formula

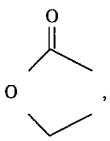

$R^3$ represents aryl having 6 to 10 carbon atoms, which is optionally substituted up to 3 times by identical or different substituents from the group consisting of halogen, nitro, cyano, hydroxyl, amino, trifluoromethyl, trifluoromethoxy, trifluoromethylthio, straight-chain or branched alkyl, alkoxy or alkoxycarbonyl in each case having up to 8 carbon atoms and carboxyl, or represents thienyl or pyridyl, each of which is optionally substituted by halogen, $R^4$ represents a group of the formula $-CO-NR^{12}R^{13}$, $-CO-A-R^{14}$ or $-P(O)(OR^{15})(OR^{16})$, in which $R^{12}$ and $R^{13}$ are identical or different and denote hydrogen or a straight-chain, branched, cyclic, saturated or unsaturated hydrocarbon radical having up to 10 carbon atoms, which is optionally substituted by cycloalkyl having 3 to 8 carbon atoms, halogen, hydroxyl, cyano or by aryl, aryloxy or arylthio in each case having 6 to 10 carbon atoms or by a 5- to 7-membered, saturated or unsaturated heterocycle having up to 3 heteroatoms from the group consisting of S, N and O, where the cycles for their part can be substituted by halogen, cyano or by straight-chain or branched alkyl, alkoxy, alkylthio, alkoxycarbonyl, halogenoalkyl, halogenoalkoxy or halogenoalkylthio in each case having up to 4 carbon atoms, or denote aryl having 6 to 10 carbon atoms or a 5- to 7-membered, saturated or unsaturated heterocycle having up to 3 heteroatoms from the group consisting of S, N and O, each of which is optionally substituted up to 2 times by identical or different substituents from the group consisting of halogen and cyano or by straight-chain or branched alkyl, alkoxy, alkylthio, alkoxycarbonyl, halogenoalkyl, halogenoalkoxy or halogenoalkylthio in each case having up to 4 carbon atoms, or $R^{12}$ and $R^{13}$ together, including the nitrogen atom, form a 5- to 8-membered, saturated or unsaturated heterocycle which is optionally interrupted by an oxygen atom or by a radical of the formula $S(O)_b$, $-CO-$ or $-NR^{17}$, in which $b$ denotes a number 0, 1 or 2, $R^{17}$ denotes hydrogen or aryl having 6 to 10 carbon atoms, which is optionally substituted up to 2 times by identical or different substituents from the group consisting of halogen and cyano or by straight-chain or branched alkyl, alkoxy, alkylthio, alkoxycarbonyl, halogenoalkyl, halogenoalkoxy or halogenoalkylthio in each case having up to 4 carbon atoms, or denotes a cyclic, straight-chain or branched, saturated or unsaturated hydrocarbon radical having up to 8 carbon atoms, which is optionally substituted by hydroxyl or halogen or by aryl having 6 to 10 carbon atoms or a 5- to 7-membered, saturated or unsaturated heterocycle having 3 heteroatoms from the group consisting of S, N and O, which for their part can be substituted up to 2 times by identical or different substituents from the group consisting of halogen and cyano or by straight-chain or branched alkyl, alkoxy, alkylthio, alkoxycarbonyl, halogenoalkyl, halogenoalkoxy or halogenoalkylthio in each case having up to 4 carbon atoms, and the heterocycle is optionally substituted by straight-chain or branched alkoxy or alkylthio in each case having up to 4 carbon atoms, halogen, aryl having 6 to 10 carbon atoms, a 4- to 7-membered, saturated or unsaturated heterocycle having up to 3 heteroatoms from the group consisting of S, N and O or by straight-chain or branched alkyl having up to 4 carbon atoms, which for its part can optionally be substituted by aryl having 6 to 10 carbon atoms, A denotes a direct bond or an oxygen atom, $R^{14}$ denotes hydrogen or aryl having 6 to 10 carbon atoms or a 4- to 7-membered, saturated or unsaturated heterocycle having up to 3 heteroatoms from the group consisting of S, N and O, each of which is optionally substituted up to 3 times by identical or different substituents from the group consisting of halogen and cyano or by straight-chain or branched alkyl, alkoxy, alkylthio, alkoxycarbonyl, halogenoalkyl, halogenoalkoxy or halogenoalkylthio in each case having up to 4 carbon atoms, or denotes a cyclic, straight-chain or branched, saturated or unsaturated hydrocarbon radical having up to 12 carbon atoms, which is optionally interrupted up to 3 times by identical or different oxygen or —CO—, —CO—NH—, —O—CO—, —CO—O—, —NH—CO—, —SO$_2$—NH—, —NH—SO$_2$—, —S(O)$_c$— or —NR$^{18}$, in which c has the abovementioned meaning of b and is identical to or different from this, $R^{18}$ has the abovementioned meaning of $R^{17}$ and is identical to or different from this, or the hydrocarbon radical is optionally interrupted up to 3 times by identical or different aralkylidene having 6 to 10 carbon atoms or a cyclic radical of the formula

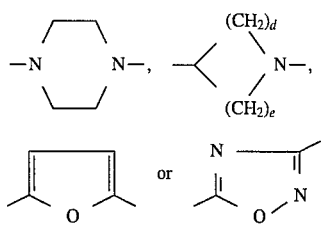

in which d and e are identical or different and denote a number 1 or 2, and in which aralkylidene and the heterocycles for their part can be substituted by halogen, cyano or by straight-chain or branched alkyl, alkoxy, alkylthio, alkoxycarbonyl, halogenoalkyl, halogenoalkoxy or halogenoalkylthio in each case having up to 4 carbon atoms, and where the hydrocarbon radical is optionally substituted up to 3 times by identical or different substituents from the group consisting of cycloalkyl having 3 to 8 carbon atoms, halogen, nitro, cyano, hydroxyl and —O—NO$_2$, straight-chain or branched alkylthio, alkoxy or acyloxy in each case having up to 8 carbon atoms, or by aryl, aryloxy or arylthio in each case having 6 to 10 carbon atoms or by a 5- to 7-membered, saturated or unsaturated heterocycle having up to 3 heteroatoms from the group consisting of S, N and O, where the cycles for their part can be substituted up to 3 times by identical or different substituents from the group consisting of halogen and cyano or by straight-chain or branched alkyl, alkoxy, alkylthio, alkoxycarbonyl, halogenoalkyl, halogenoalkoxy or halogenoalkylthio in each case having up to 4 carbon atoms, or the hydrocarbon radical is substituted by a group of the formula —CO$_2$—R$^{19}$, —CONR$_{20}$R$^{21}$ or —NR$^{22}$R$^{23}$, in which $R^{19}$ has the abovementioned meaning of $R^{17}$ and is identical to or different from this
and $R^{20}$, $R^{21}$, $R^{22}$ and $R^{23}$ have the abovementioned meaning of $R^{12}$ and $R^{13}$ and are identical to or different from these, $R^{15}$ and $R^{16}$ are identical or different and denote straight-chain or branched alkyl having up to 8 carbon atoms, or $R^{15}$ and $R^{16}$ together, including the oxygen atoms and the phosphorus, form a 5- to 7-membered, saturated heterocycle, and their salts, with the proviso that $R^5$ must not represent unsubstituted alkyl if $R^1$ simultaneously denotes unsubstituted alkyl or $R^1$ and $R^2$ together form a lactone ring.

Physiologically acceptable salts can be salts of the compounds according to the invention with inorganic or organic acids. Preferred salts are those with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, lactic acid, benzoic acid or methanesulphonic acid, ethanesulphonic acid, benzenesulphonic acid, toluenesulphonic acid or naphthalenedisulphonic acid.

The compounds according to the invention exist in stereoisomeric forms which behave either as image and mirror image (enantiomers), or which do not behave as image and mirror image (diastereomers). The invention relates both to the antipodes and to the racemic forms as well as to the diastereomer mixtures. Like the diastereomers, the racemic forms can be separated into the stereoisomerically homogeneous constituents in a known manner.

Preferred compounds of the general formula (I) are those in which $R^1$ and $R^5$ are identical or different and represent hydrogen, cyano, formyl, trifluoromethyl or straight-chain or branched alkyl having up to 6 carbon atoms, which is optionally substituted by hydroxyl, straight-chain or branched alkoxy or alkoxycarbonyl in each case having up to 4 carbon atoms or by a group of the formula —NR$^6$R$^7$, —O—CO—R$^8$, —O—(CH$_2$)$_a$—OR$^{8'}$ or —O—(CH$_2$)$_{a'}$, —NR$^9$R$^{10}$, in which $R^6$, $R^7$, $R^9$ and $R^{10}$ are identical or different and denote hydrogen, phenyl or straight-chain or branched alkyl having up to 4 carbon atoms, $R^8$ and $R^{8'}$ are identical or different and denote straight-chain or branched alkyl having up to 4 carbon atoms, and a and a' are identical or different and denote a number 2, 3 or 4, $R^2$ represents nitro, cyano or formyl, or $R^1$ and $R^2$ together form a lactone ring of the formula

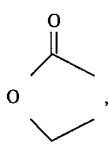

$R^3$ represents phenyl which is optionally substituted by fluorine, chlorine, nitro, cyano, hydroxyl, amino or trifluoromethyl or by straight-chain or branched alkyl or alkoxy in each case having up to 4 carbon atoms, or represents thienyl or pyridyl, each of which is optionally substituted by fluorine, chlorine or bromine, $R^4$ represents a group of the formula $-CO-NR^{12}R^{13}$, $-CO-A-R^{14}$ or $-P(O)(OR^{15})(OR^{16})$, in which $R^{12}$ and $R^{13}$ are identical or different and denote hydrogen or a straight-chain or branched, cyclic, saturated or unsaturated hydrocarbon radical having up to 6 carbon atoms, which is optionally substituted by cyclopropyl, cyclopentyl, cyclohexyl, fluorine, chlorine, bromine or hydroxyl or by phenyl or pyridyl, where the cycles for their part can be substituted by fluorine, chlorine or cyano or by straight-chain or branched alkyl, alkoxy, alkylthio, alkoxycarbonyl in each case having up to 3 carbon atoms, trifluoromethyl or trifluoromethoxy, or denote phenyl or pyridyl, each of which is optionally substituted by fluorine or chlorine or by straight-chain or branched alkyl, alkoxy, alkylthio, alkoxycarbonyl in each case having up to 4 carbon atoms, trifluoromethyl or trifluoromethoxy, or $R^{12}$ and $R^{13}$ together, including the nitrogen atom, form a 5- to 7-membered, saturated or unsaturated heterocycle which can optionally be interrupted by oxygen or by a radical of the formula $S(O)_b$, $-CO-$ or $-NR^{17}$, in which b denotes a number 0, 1 or 2, $R^{17}$ denotes hydrogen or phenyl, or denotes a cyclic, straight-chain or branched, saturated or unsaturated hydrocarbon radical having up to 6 carbon atoms, which is optionally substituted by fluorine, chlorine or bromine, or by phenyl or pyridyl which for their part can be substituted by fluorine, chlorine, methyl, ethyl, methoxy, ethoxy, trifluoromethyl or trifluoromethoxy, and the heterocycle is optionally substituted by straight-chain or branched alkoxy or alkylthio in each case having up to 3 carbon atoms, fluorine, chlorine, bromine, phenyl or pyridyl or by branched alkyl having up to 4 carbon atoms or benzyl, A denotes a direct bond or an oxygen atom, $R^{14}$ denotes hydrogen, phenyl or pyridyl, each of which is optionally substituted by fluorine or chlorine or by straight-chain or branched alkyl, alkoxy or alkylthio in each case having up to 3 carbon atoms, trifluoromethyl or trifluoromethoxy, or denotes a cyclic, straight-chain or branched, saturated or unsaturated hydrocarbon radical having up to 10 carbon atoms, which is optionally interrupted up to 2 times by identical or different oxygen or $-CO-$, $-CO-NH-$, $-O-CO-$, $-CO-O-$, $-NH-CO-$, $-SO_2-NH-$, $-NH-SO_2-$, $-S(O)_c-$ or $-NR^{18}$, in which c has the abovementioned meaning of b and is identical to or different from this, $R^{18}$ has the abovementioned meaning of $R^{17}$ and is identical to or different from this, or the hydrocarbon radical is optionally interrupted up to 2 times by identical or different benzylidene or a cyclic radical of the formula

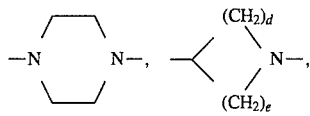

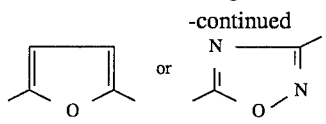

in which d and e are identical or different and denote a number 1 or 2, and where the hydrocarbon radical is optionally substituted up to 2 times by identical or different substituents from the group consisting of cyclopropyl, cyclobutyl, cyclopentyl, cyclohexyl, fluorine, chlorine, bromine, nitro, cyano, hydroxyl, $-O-NO_2$ and straight-chain or branched alkylthio, alkoxy or acyloxy in each case having up to 6 carbon atoms or by phenyl, phenoxy, phenylthio or pyridyl, where the cycles for their part are substituted up to 2 times by identical or different substituents from the group consisting of fluorine, chlorine, bromine and cyano or by straight-chain or branched alkyl, alkoxy, alkylthio, alkoxycarbonyl in each case having up to 4 carbon atoms, trifluoromethyl or trifluoromethoxy, or the hydrocarbon radical is substituted by a group of the formula $-CO_2-R^{19}$, $-CONR^{20}R^{21}$ or $-NR^{22}R^{23}$, in which $R^{19}$ has the abovementioned meaning of $R^{17}$ and is identical to or different from this and $R^{20}$, $R^{21}$, $R^{22}$ and $R^{23}$ have the abovementioned meaning of $R^{12}$ and $R^{13}$ and are identical to or different from these, $R^{15}$ and $R^{16}$ are identical or different and denote straight-chain or branched alkyl having up to 6 carbon atoms or $R^{15}$ and $R^{16}$ including the oxygen atoms and the phosphorus, form a 6-membered saturated cycle, and their salts, with the proviso that $R^5$ must not represent unsubstituted alkyl if $R^1$ simultaneously denotes unsubstituted alkyl or $R^1$ and $R^2$ together form a lactone ring.

Particularly preferred compounds of the general formula (I) are those in which $R^1$ and $R^5$ are identical or different and represent hydrogen, cyano, formyl, trifluoromethyl or methyl or ethyl, each of which is optionally substituted by hydroxyl, straight-chain or branched alkoxy or alkoxycarbonyl in each case having up to 4 carbon atoms or by a group of the formula $-NR^6R^7$, $-O-CO-R^8$, $-O-(CH_2)_a-OR^{8'}$ or $-O-(CH_2)_a-NR^9R^{10}$, in which $R^6$, $R^7$, $R^9$ and $R^{10}$ are identical or different and denote hydrogen, methyl or alkyl having 1–4 C atoms, $R^8$ and $R^{8'}$ are identical or different and denote alkyl having 1–4 C atoms, and a and a' are identical or different and denote a number 2 or 3, $R^2$ represents nitro, cyano or formyl, or $R^1$ and $R^2$ together form a lactone ring of the formula

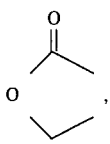

$R^3$ represents phenyl which is optionally substituted by fluorine, chlorine, nitro, trifluoromethyl, alkyl or alkoxy having up to 4 carbon atoms, $R^4$ represents a group of the formula —CO—NR$^{12}$R$^{13}$ or —CO—A—R$^{14}$, in which $R^{12}$ and $R^{13}$ are identical or different and denote hydrogen or phenyl or a straight-chain, branched, cyclic, saturated or unsaturated hydrocarbon radical having up to 4 carbon atoms, which is optionally substituted by phenyl which for its part can be substituted by fluorine, chlorine, or alkyl or alkoxy having up to 4 C atoms, A denotes a direct bond or an oxygen atom, $R^{14}$ denotes hydrogen or phenyl, or denotes a cyclic, straight-chain or branched, saturated or unsaturated hydrocarbon radical having up to 8 carbon atoms, which is optionally interrupted by oxygen or sulphur or by —CO—NH—, —O—CO—, —CO—O—, —NH—CO— or —NR$^{18}$, in which $R^{18}$ denotes hydrogen, phenyl or straight-chain or branched alkyl having up to 4 carbon atoms, which is optionally substituted by phenyl, and where the hydrocarbon radical is optionally substituted by cyclopropyl, cyclobutyl, cyclopentyl, cyclohexyl, fluorine, chlorine, cyano, hydroxyl, phenyl, phenoxy, phenylthio or pyridyl, or is substituted by a group of the formula —CO$_2$—R$^{19}$, —CONR$^{20}$R$^{21}$ or —NR$^{22}$R$^{23}$, in which $R^{19}$ has the abovementioned meaning of $R^{18}$ and is identical to or different from this and $R^{20}$, $R^{21}$, $R^{22}$ and $R^{23}$ have the abovementioned meaning of $R^{12}$ and $R^{13}$ and are identical to or different from these, and their salts, with the proviso that $R^5$ must not represent unsubstituted alkyl if $R^1$ simultaneously denotes unsubstituted alkyl or $R^1$ and $R^2$ together form a lactone ring.

Very particularly preferred compounds of the general formula (I) are those in which $R^1$ and $R^5$ are identical or different and represent hydrogen, formyl, cyano, trifluoromethyl or methyl which is optionally substituted by hydroxyl, methoxy, acetoxy, amino or by a radical of the formula O—(CH$_2$)$_a$—OCH$_3$ or —O—(CH$_2$)$_{a'}$—NH$_2$, in which a and a' are identical or different and denote a number 2 or 3, $R^2$ represents nitro or cyano or $R^1$ and $R^2$ together form a lactone ring of the formula

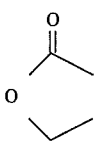

$R^3$ represents phenyl which is optionally substituted by fluorine, chlorine, nitro, trifluoromethyl, methyl or methoxy, $R^4$ represents a group of the formula —CO—A—R$^{14}$, in which A denotes a direct bond or an oxygen atom and $R^{14}$ denotes a straight-chain or branched, saturated hydrocarbon radical having up to 6 carbon atoms, which is optionally interrupted by oxygen and which is optionally substituted by cyclopropyl, cyclobutyl, cyclopentyl, cyano, phenyl, pyridyl or phenoxy, or is substituted by a group —NR$^{22}$R$^{23}$, in which $R^{22}$ and $R^{23}$ are identical or different and denote hydrogen, straight-chain or branched alkyl having up to 4 carbon atoms, phenyl or benzyl, and their salts, with the proviso that $R^5$ must not represent unsubstituted alkyl if $R^1$ simultaneously denotes unsubstituted alkyl or $R^1$ and $R^2$ together form a lactone ring.

The invention also relates to processes for the preparation of the compounds of the general formula (I) according to the invention, characterized in that in the case where $R^1$ and $R^2$ have the abovementioned meaning but do not together form a lactone ring,

[A] compounds of the general formula (II)

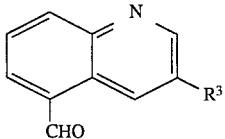

(II)

in which $R^3$ has the abovementioned meaning, are first reacted with acyl derivatives of the general formula (III)

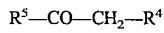

$R^5$—CO—CH$_2$—R$^4$ (III)

in which $R^4$ and $R^5$ have the abovementioned meaning, if appropriate with isolation of the corresponding ylidene compounds of the general formula (IV)

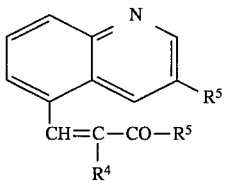

(IV)

in which $R^3$, $R^4$ and $R^5$ have the abovementioned meaning, and then reacted either with compounds of the formula (V)

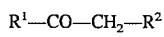

$R^1$—CO—CH$_2$—R$^2$ (V)

in which

R$^1$ and R$^2$ have the abovementioned meaning, in the presence of ammonia or ammonium salts, or directly with amino derivatives of the general formula (VI)

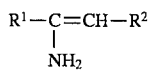   (VI)

in which

R$^1$ and R$^2$ have the abovementioned meaning, if appropriate in the presence of inert organic solvents, or

[B] the aldehydes of the general formula (II) are first reacted with the compounds of the general formula (V), optionally with isolation of the ylidene compounds of the general formula (VII)

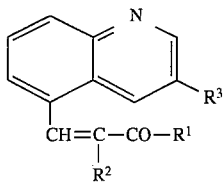   (VII)

in which

R$^1$, R$^2$ and R$^3$ have the abovementioned meaning, and in a next step reacted with the abovementioned compounds of the general formula (III) in inert solvents, in the presence of ammonia or ammonium salts or directly with enaminocarboxylic acid derivatives of the general formula (VIII)

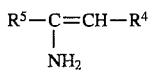   (VIII)

in which

R$^4$ and R$^5$ have the abovementioned meaning, or in the case where R$^1$ and R$^2$ together form a lactone ring,

[C] first, according to the methods mentioned in [A] and [B], compounds of the general formula (IX)

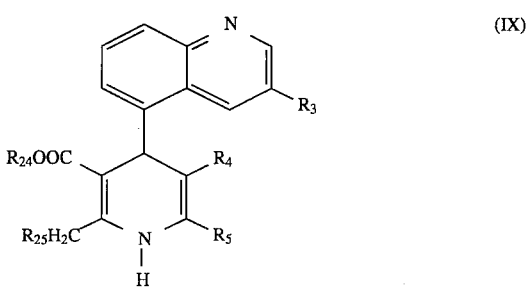   (IX)

in which

R$^3$, R$^4$ and R$^5$ have the abovementioned meaning,

R$^{24}$ represents a C$_1$–C$_6$ -alkyl radical and

R$^{25}$ represents a customary leaving group, are prepared and an acid- or base-catalyzed ring closure is added according to customary processes.

The processes according to the invention can be illustrated by the following reaction scheme:

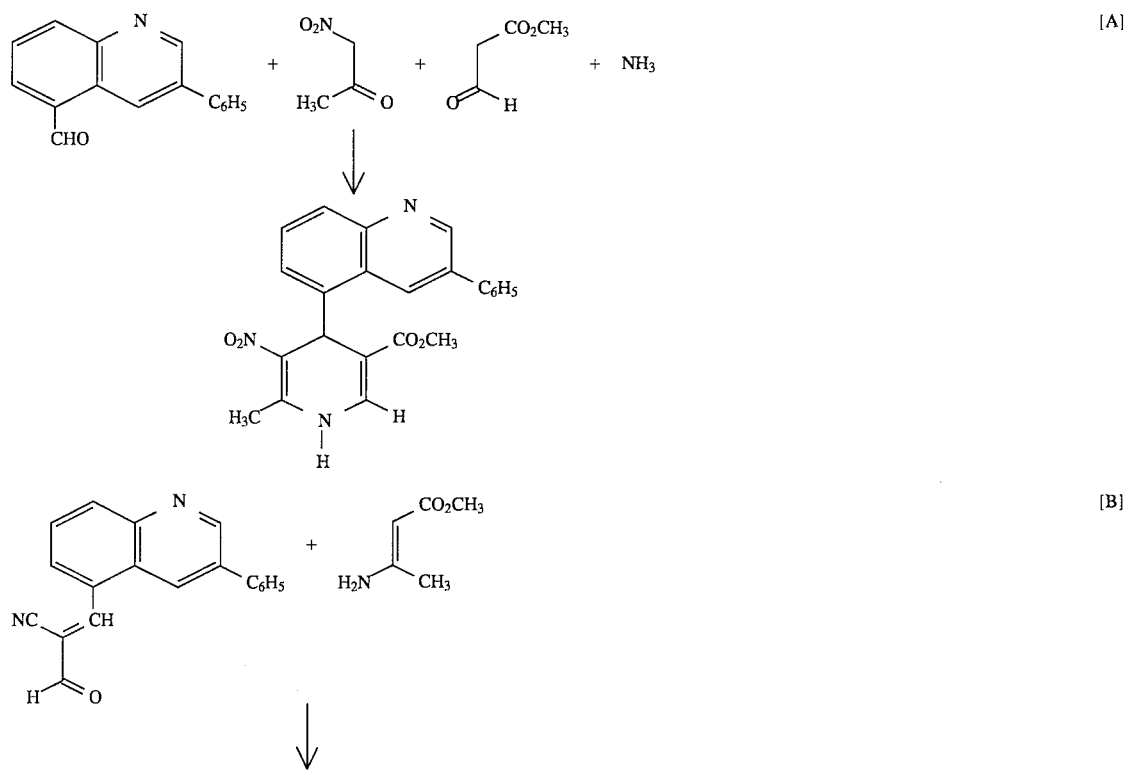

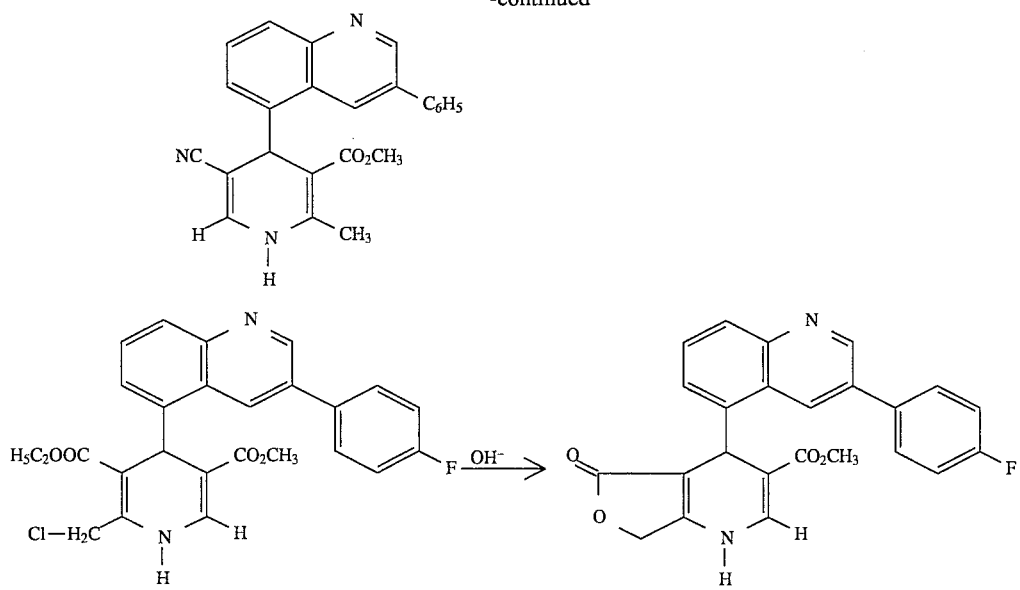

Suitable solvents or processes [A], [B] and [C] are all inert organic solvents. These preferably include alcohols such as methanol, ethanol, n- or iso-propanol, ethers such as diethyl ether, tetrahydrofuran, dioxane or glycol monomethyl ether or glycol dimethyl ether, glacial acetic acid, pyridine, dimethylformamide, dimethyl sulphoxide, acetonitrile or hexamethylphosphoramide, toluene or alkyl acetates.

The reaction temperature for processes [A], [B] and [C] can be varied within a substantial range. In general, the reaction is carried out in a range from 10° C. to 200° C., preferably from 20° C. to 150° C.

The processes can be carried out at normal pressure, elevated pressure or reduced pressure (for example from 0.5 to 5 bar), preferably at normal pressure.

When carrying out the process according to the invention, any desired ratio of the substances participating in the reaction can be used. In general, however, the reaction is carried out using molar amounts of the reactants.

Enantiomerically pure forms are obtained e.g. by separating diastereomer mixtures of the compounds of the general formula (I), in which $R^4$ represents an optical ester radical, by a customary method, then preparing the enantiomerically pure carboxylic acids and then converting into the enantiomerically pure dihydropyridine-carboxylic acid esters, for example by esterification with appropriate alcohols.

Suitable chiral ester radicals are all esters of enantiomerically pure alcohols such as, for example, 2-butanol, 1-phenylethanol, lactic acid, lactic acid esters, mandelic acid, mandelic acid esters, 2-amino-alcohols, sugar derivatives, and many other enantiomerically pure alcohols.

The diastereomers are in general separated either by fractional crystallization, by column chromatography or by Craig partition. Which is the optimum process must be decided from case to case, sometimes it is also expedient to use combinations of the individual processes. Separation by crystallization or Craig partition or a combination of both processes is particularly suitable.

The aldehydes of the general formula (II) are known in some cases [German Offenlegungsschrift 4,011,105] or can be prepared by customary methods.

The compounds of the general formulae (III), (IV), (V), (VI), (VII), (VIII) and (IX) are known or can also be prepared by customary methods.

The above preparation processes are only given for clarification. The preparation of the compounds of the formula (I) is not restricted to these processes, but any modification of these processes can be used in the same manner for the preparation of the compounds according to the invention.

The compounds according to the invention show an unforeseeable, useful spectrum of pharmacological action. They affect the contractility of the heart and the tone of the smooth musculature.

They can therefore be employed in medicaments for affecting pathologically modified blood pressure, as coronary therapeutics and for the treatment of cardiac insufficiency. They can moreover be used for the treatment of cardiac arrhythmias, for lowering the blood sugar, for the detumescence of mucous membranes and for affecting the salt and liquid balance.

The cardiac and vascular effects were found in the isolated perfused guinea-pig heart. To this end, the hearts of guinea pigs of 250 to 350 g in weight are used. The animals are killed by a blow to the head, the thorax is opened, and a metal cannula is tied into the exposed aorta. The heart is separated from the thorax with the lungs and attached via an aortic cannula to the perfusion apparatus with continuous perfusion. The lungs are separated at the lung roots. The perfusion medium used is a Krebs-Henseleit solution (118.5 mmol/l of NaCl, 4.75 mmol/l of KCl, 1.19 mmol/l of $KH_2PO_4$, 1.19 mmol/l of $MgSO_4$, 25 mmol/l of $NaHCO_3$, 0.013 mmol/l of $Na_2EDTA$), whose $CaCl_2$ content is 1.2 mmol/l. 10 mmol/l of glucose are added as an energy-producing substrate. Before perfusion, the solution is filtered free of particles. The solution is aerated with 95% $O_2$, 5% $CO_2$ to maintain the pH 7.4. The hearts are perfused under constant flow (10 ml/min) at 32° C. by means of a peristaltic pump.

To measure the cardiac function, a liquid-filled latex balloon which is connected to a pressure transducer via a liquid column is introduced into the left ventricle through the left auricle, and the isovolumetric contractions are recorded on a rapid recorder. The perfusion pressure is recorded by means of a pressure transducer which is connected to the perfusion system upstream of the heart. Under these conditions, a reduction in the perfusion pressure indicates a coronary dilation, an increase or decrease in the left-ventricular contraction amplitude a reduction or an increase in cardiac contractility. The compounds according to the invention are perfused, in suitable dilutions, into the perfusion system shortly upstream of the isolated heart.

The new active compounds can be converted in a known manner into the customary formulations, such as tablets, coated tablets, pills, granules, aerosols, syrups, emulsions, suspensions and solutions, using inert, nontoxic, pharmaceutically suitable excipients or solvents. In this case, the therapeutically active compound should in each case be present in a concentration of about 0.5 to 90% by weight of the total mixture, i.e. in amounts which are sufficient in order to achieve the dosage range indicated.

The formulations are prepared, for example, by extending the active compounds with solvents and/or excipients, if appropriate, using emulsifiers and/or dispersants, where e.g. in the case of the use of water as a diluent organic solvents can optionally be used as auxiliary solvents.

Administration is carried out in the customary manner, preferably orally or parenterally, in particular perlingually or intravenously.

In general, it has proven advantageous in the case of intravenous administration to administer amounts of about 0.001 to 1 mg/kg, preferably about 0.01 to 0.5 mg/kg of body weight to achieve effective results, and in the case of oral administration the dose is about 0.01 to 20 mg/kg, preferably 0.1 to 10 mg/kg of body weight.

In spite of this, it may sometimes be necessary to depart from the amounts mentioned, in particular depending on the body weight or the type of administration route, on individual behaviour towards the medicament, the manner of its formulation and the time or interval at which administration takes place. Thus, in some cases it may be sufficient to manage with less than the abovementioned minimum amount, while in other cases the abovementioned upper limit must be exceeded. In the case of the administration of relatively large amounts, it may be advisable to divide these into several individual doses over the course of the day.

EXAMPLE 1

Propyl 3-cyano-6-methyl-4-(3-phenylquinolin-5-yl)-1,4-dihydropyridine-5-carboxylate

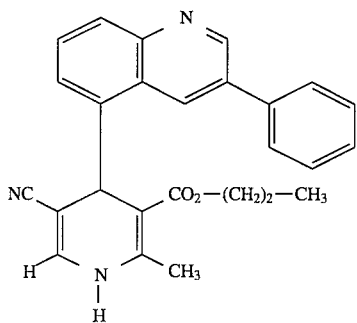

2.33 g (10 mmol) of 3-phenylquinoline-5-carbaldehyde are treated in 20 ml of n-propanol with 0.69 g (10 mmol) of isoxazole. A solution of 0.23 g (10 mmol) of sodium in 6 ml of n-propanol is added dropwise to this suspension. The mixture is stirred at 40° C. for 4 hours, treated with 1.43 g (10 mmol) of propyl 3-aminocrotonate and 0.6 ml (10 mmol) of acetic acid and heated to reflux for 24 h. It is cooled and concentrated, and the residue is taken up in ethyl acetate/water. The aqueous phase is separated off, and the ethyl acetate phase is washed with water, dried and concentrated. The crude product obtained is purified by flash chromatography using toluene/ethyl acetate mixtures. After crystallization with acetonitrile, 1.4 g of colourless crystals of melting point 217°–218° C. are obtained.

EXAMPLE 2

(Intermediate for Example 3)
Ethyl 3-acetyl-6-acetoxymethyl-4-(3-phenylquinolin-5-yl)-1,4-dihydropyridine-5-carboxylate

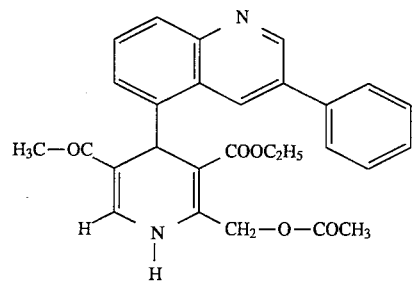

2.017 g (5 mmol) of ethyl 2-(3-phenylquinol-5-ylmethylene)-4-acetoxy-3-oxo-butyrate are boiled with 0.47 g (5.5 mmol) of 4-amino-3-buten-2-one and 0.33 ml of acetic acid in 40 ml of isopropanol for 24 hours. The mixture is cooled, and the precipitated crystals are filtered off with suction and washed with isopropanol. 0.76 g of the intermediate of melting point 234°–235° C. are obtained.

Example 3

3-Acetyl-4-(3-phenylquinolin-5-yl)-5-oxo-1,4,5,7-tetrahydrofuro[3,4-b]pyridine

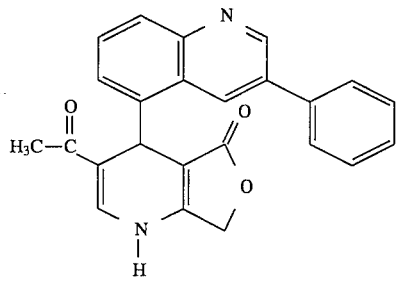

476 mg of the compound from Example 2 are treated in 12 ml of methanol with 9.25 mg of potassium hydroxide and the mixture is heated to boiling for 2 hours. It is cooled and rendered neutral by dropwise addition of 1 N hydrochloric acid. The crystalline product is filtered off with suction and washed with methanol/water. 310 mg of colourless crystals of melting point 204°–205° C. are obtained.

The examples shown in Table 1 are prepared in analogy to the procedures of Examples 1, 2 and 3:

TABLE 1

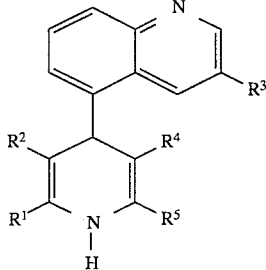

| Ex. No. | $R^1$ | $R^2$ | $R^4$ | $R^5$ | $R^{26}$ | m.p. °C. |
|---|---|---|---|---|---|---|
| 4 | $-CH_2O-CH_3$ | $-NO_2$ | $-CO_2CH_3$ | $-CH_3$ | H | 115 |
| 5 | $-CH_2-O-(CH_2)_2-OCH_3$ | $-NO_2$ | $-CO_2CH_3$ | $-CH_3$ | H | |
| 6 | $-CH_3$ | $-CN$ | $-CO_2C_2H_5$ | $-CH_2-O-CO-CH_3$ | H | 186 |
| 7 | $-CH_3$ | $-CN$ | $-CO_2C_2H_5$ | $-CH_2-O-CO-CH_3$ | Cl | 120 |
| 8 | $-CH_3$ | $-CN$ | $-COCH_3$ | H | F | 262 |

| Ex.No. | $R^1$ | $R^2$ | $R^4$ | $R^5$ | $R^{26}$ | m.p. °C. | Enantiomer |
|---|---|---|---|---|---|---|---|
| 9  | $-CH_3$ | $-CN$ | $-CO-CH_3$ | H | H | 278 | |
| 10 | $-CH_3$ | $-CN$ | $-CO_2-CH_3$ | H | H | | |
| 11 | H | $-CN$ | $-CO_2-(CH_2)_2-CH_3$ | $-CH_3$ | H | 171–173 | (−) |
| 12 | H | $-CN$ | $-CO_2-(CH_2)_2-CH_3$ | $-CH_3$ | H | 171–174 | (+) |
| 13 | $-CH_3$ | $-CN$ | $-CO_2CH_3$ | $-CF_3$ | H | 139 | |
| 14 | $-CH_3$ | $-CN$ | $-CO_2CH(CH_3)_2$ | $-CF_3$ | H | 212 | |
| 15 | $-CH_3$ | $-CN$ | $-CO_2C_2H_5$ | $-CF_3$ | H | 182 | |
| 16 | $-CH_3$ | $-CN$ | $-CO_2C_2H_5$ | $-CH_2NH_2$ | H | | |
| 17 | $-CH_3$ | $-CN$ | $-CO_2C_2H_5$ | $-CH_2-O(CH_2)_2-NH_2$ | H | 162 | |
| 18 | $-CH_3$ | $-CN$ | $-CO_2-CH(CH_3)_2$ | $-CH_2-O-(CH_2)_3-NH_2$ | H | foam | |

We claim:

1. A compound of the formula

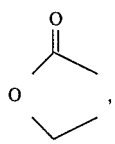

(I)

wherein $R^1$ and $R^5$ are identical or different and represent hydrogen, formyl, cyano, trifluoromethyl or methyl which is optionally substituted by hydroxyl, methoxy, acetoxy, amino or by a radical of the formula $-O-(CH_2)_a-OCH_3$ or $-O-(CH_2)_{a'}-NH_2$, in which a and a' are identical or different and denote a number 2 or 3, $R^2$ represents nitro or cyano or $R^1$ and $R^2$ together form a lactone ring of the formula $R^3$ represents phenyl which is optionally substituted by fluorine, chlorine, nitro, trifluoromethyl, methyl or methoxy, $R^4$ represents a group of the formula $-CO-A-R^{14}$, in which A denoted a direct bond or an oxygen atom and $R^{14}$ denotes a straight-chain or branched, saturated hydrocarbon radical having up to 6 carbon atoms, which is optionally interrupted by oxygen and which is optionally substituted by cyclopropyl, cyclobutyl, cyclopentyl, cyano, phenyl, pyridyl or phenoxy, or is substituted by a group $-NR^{22}R^{23}$, in which $R^{22}$ and $R^{23}$ are identical or different and denote hydrogen, straight-chain or branched alkyl having up to 4 carbon atoms, phenyl or benzyl, or a pharmaceutically acceptable salt thereof, with the proviso that $R^5$ must not represent unsubstituted alkyl if $R^1$ simultaneously denotes unsubstituted alkyl or $R^1$ and $R^2$ together form a lactone ring.

2. The compound according to claim 1 which is propyl 3-cyano-6-methyl-4(3-phenylquinolin-5-yl)-1,4-dihydropyridine-5-carboxylate.

3. A composition which comprises an effective amount of a compound according to claim 1 and a pharmaceutically acceptable carrier.

4. A compound according to claim 1, wherein $R^1$ and $R^5$ are identical or different and represent hydrogen, trifluoromethyl or methyl which is optionally substituted by methoxy, acetoxy, amino or by a radical of the formula $-O-(CH_2)_a-OCH_3$ or $-O-(CH_2)_{a'}-NH_2$, in which a and a' are identical or different and denote a number 2 or 3, $R^2$ represents nitro or cyano or $R^1$ and $R^2$ together from a lactone ring of the formula

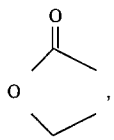

$R^3$ represents phenyl which is optionally substituted by fluorine, chlorine, nitro, trifluoromethyl, $R^4$ represents a group of the formula —CO—A—$R^{14}$, in which A denotes a direct bond or an oxygen atom and $R^{14}$ denotes a straight-chain or branched, saturated hydrocarbon radical having up to 8 carbon atoms with the proviso that $R^5$ must not represent unsubstituted alkyl if $R^1$ simultaneously denotes unsubstituted alkyl or $R^1$ and $R^2$ together form a lactone ring.

5. A method for treatment of cardiac circulatory disorders which comprises administering an effective amount of a compound of according to claim 1 to a host in need thereof.

* * * * *